(12) United States Patent
Chibber

(10) Patent No.: US 7,811,781 B2
(45) Date of Patent: Oct. 12, 2010

(54) CORE 2 β(1,6)-ACETYLGLYCOSAMINYLTRANSFERASE AS DIAGNOSTIC MARKER FOR ATHEROSCLEROSIS

(75) Inventor: Rakesh Chibber, Exeter (GB)

(73) Assignee: BTG International Limited, London (GB)

( * ) Notice: Subject to any disclaimer, the term of this patent is extended or adjusted under 35 U.S.C. 154(b) by 36 days.

(21) Appl. No.: 11/922,983

(22) PCT Filed: Jul. 6, 2006

(86) PCT No.: PCT/GB2006/002502

§ 371 (c)(1),
(2), (4) Date: Dec. 28, 2007

(87) PCT Pub. No.: WO2007/003950

PCT Pub. Date: Jan. 11, 2007

(65) Prior Publication Data
US 2009/0093006 A1    Apr. 9, 2009

(30) Foreign Application Priority Data
Jul. 6, 2005    (GB) .................................. 0513883.9

(51) Int. Cl.
C12Q 1/48    (2006.01)
G01N 33/00    (2006.01)
(52) U.S. Cl. ........................................ 435/15; 435/7.24
(58) Field of Classification Search ........................ None
See application file for complete search history.

(56) References Cited

U.S. PATENT DOCUMENTS

| | | | |
|---|---|---|---|
| 5,104,856 A | 4/1992 | Esko et al. |
| 5,360,733 A | 11/1994 | Fukuda et al. |
| 5,461,143 A | 10/1995 | Wong et al. |
| 5,486,510 A | 1/1996 | Bouic et al. |
| 5,589,182 A | 12/1996 | Tashiro et al. |
| 5,624,832 A | 4/1997 | Fukuda et al. |
| 5,658,778 A | 8/1997 | Fukuda et al. |
| 5,843,707 A | 12/1998 | Larsen et al. |
| 5,880,091 A | 3/1999 | Cummings et al. |
| 5,886,029 A | 3/1999 | Dhaliwal |
| 5,952,393 A | 9/1999 | Sorkin, Jr. |
| 5,958,770 A | 9/1999 | Cham et al. |
| 5,965,449 A | 10/1999 | Novak |
| 5,985,936 A | 11/1999 | Novak |
| 6,042,834 A | 3/2000 | Baraka |
| 6,087,353 A | 7/2000 | Stewart et al. |
| 6,131,578 A | 10/2000 | King et al. |
| 6,197,832 B1 | 3/2001 | Sorkin, Jr. |
| 6,346,267 B1 | 2/2002 | Fry et al. |
| 6,383,514 B1 | 5/2002 | Weitkemper et al. |
| 6,407,085 B1 | 6/2002 | Kief |
| 6,635,461 B1 | 10/2003 | Schwientek et al. |
| 6,787,151 B2 | 9/2004 | Meijer et al. |
| 6,933,291 B2 | 8/2005 | Qi et al. |
| 6,998,501 B1 | 2/2006 | Wright et al. |
| 2002/0018811 A1 | 2/2002 | Penteado et al. |
| 2002/0098563 A1 | 7/2002 | Korczak et al. |
| 2002/0156051 A1 | 10/2002 | Kutney et al. |
| 2002/0183294 A1 | 12/2002 | Barraclough et al. |
| 2002/0193317 A1 | 12/2002 | Xia et al. |
| 2003/0004147 A1 | 1/2003 | Barraclough et al. |
| 2003/0096316 A1 | 5/2003 | Wester |
| 2004/0033521 A1 | 2/2004 | Korczak et al. |
| 2004/0038923 A1 | 2/2004 | Marth et al. |
| 2004/0049352 A1 | 3/2004 | Andre et al. |
| 2004/0203111 A1 | 10/2004 | Schwientek et al. |
| 2004/0220115 A1 | 11/2004 | Cham |
| 2004/0249138 A1 | 12/2004 | Lawson |
| 2006/0052351 A1 | 3/2006 | Platt et al. |
| 2007/0254847 A1 | 11/2007 | Liu et al. |

FOREIGN PATENT DOCUMENTS

| | | |
|---|---|---|
| CA | 2186987 | 6/2000 |
| CA | 2 335 436 | 8/2001 |
| CN | 1237583 A | 12/1999 |
| CN | 1243129 A | 2/2000 |
| CN | 1361111 A | 7/2002 |
| EP | 1 316 608 A1 | 6/2003 |
| EP | 0 850 243 B1 | 10/2003 |

(Continued)

OTHER PUBLICATIONS

Nielson, C and Lange, T. Blood Glucose and Heart Failure in Nondiabetic Patients; Diabetes Care, vol. 28, No. 3 (2005) pp. 607-611.*
Nishio et al. Identification and Characterization of a Gene Regulating Enzymatic Glycosylation Which is Induced by Diabetes and Hyperglycemia Specifically in Rat Cardiac Tissue; Journal of Clinical Investigation, vol. 96 (1995) pp. 1759-1767.*
Koya et al. Overexpression of Core 2 N-Acetylglycosaminyltransferase Enhances Cytokine Actions and Induces Hypertrophic Myocardium in Transgenic Mice; The FASEB Journal, vol. 13 (1999) pp. 2329-2337.*
Chibber et al. Activity of the Glycosylating Enzyme, Core 2 GLCNAC (BETA1,6) Transferase, is Higher in Polymorphonuclear Leukocytes From Diabetic Patients Compared With Age-Matched Control Subjects; Diabetes, vol. 49 (2000) pp. 1724-1730.*

(Continued)

*Primary Examiner*—Rebecca E. Prouty
*Assistant Examiner*—Paul C. Martin
(74) *Attorney, Agent, or Firm*—Nixon & Vanderhye

(57) ABSTRACT

A method of indicating the presence of the atherosclerosis (particularly coronary artery atherosclerosis) in a subject is provided, comprising comparing the level of Core 2 GlcNAc-T in a tissue sample from a subject with a reference level determined for the same tissue. A level of Core 2 GlcNAc-T in the tissue sample from a subject that is higher than that of the reference level being indicative that the subject is afflicted with atherosclerosis (particularly coronary artery atherosclerosis—coronary artery disease—CAD). In preferred embodiments, the sample consists of leukocytes and the protein level is determined as the enzymatic activity using radiolabeled UDP-GlcNAc and a Galβ(1,3)-GalNAc derivative.

7 Claims, 1 Drawing Sheet

FOREIGN PATENT DOCUMENTS

| | | |
|---|---|---|
| EP | 1 800 685 A1 | 6/2007 |
| RU | 2 027 434 C1 | 1/1995 |
| WO | WO 97/06176 A2 | 2/1997 |
| WO | WO 98/06405 A1 | 2/1998 |
| WO | WO 99/39715 A1 | 8/1999 |
| WO | WO 99/53925 A1 | 10/1999 |
| WO | WO 00/31109 | 6/2000 |
| WO | WO 00/52029 A1 | 9/2000 |
| WO | WO 00/78789 A1 | 12/2000 |
| WO | WO 01/83717 A2 | 11/2001 |
| WO | WO 02/24212 A1 | 3/2002 |
| WO | WO 02/069980 A2 | 9/2002 |
| WO | WO 02/087548 A1 | 11/2002 |
| WO | WO 03/075931 A1 | 9/2003 |
| WO | WO 2004/002497 A1 | 1/2004 |
| WO | WO 2004/029068 A1 | 4/2004 |
| WO | WO 2004/048938 A2 | 6/2004 |
| WO | WO 2004/111196 A2 | 12/2004 |

OTHER PUBLICATIONS

Notification Concerning Transmittal of International Preliminary Report on patentability; Int'l Application No. PCT/GB2006/002502; Int'l Filing Date Jul. 6, 2006, mailed Jan. 17, 2008 (9 pgs).

Battistini, L. et al; "CD8+ T cells from patients with acute multiple sclerosis display selective increase of adhesiveness in brain venules: a critical role for P-selectin glycoprotein ligand-1", Blood, vol. 101 No. 12, 4775-4780 (2003).

Ben-Mahmud, Bahaedin M., et al; "Tumor Necrosis Factor-α in Diabetic Plasma Increases the Activity of Core 2 GLcNAc-T and Adherence of Human Leukocytes to Retinal Endothelial Cells"; Diabetes, vol. 53, 2968-2976 (2004).

Brockhausen, I., et al; "Biosynthesis of O-Glycans in Leukocytes from Normal Donors and from Patients with Leukemia: Increase in O-Glycan Core 2 UDP-GlcNAc:Galβ1-3GalNAc-R (GlcNAc to GalNAc)β1(1-6)-N-Acetylglucosaminyltransferase in Leukemic Cells"; Cancer Research; 51, 1257-1263 (1991).

Buerke, Michael, et al; "Sialyl Lewis$^x$—Containing Oligosaccharide Attenuates Myocardial Reperfusion Injury in Cats"; J. Clin. Invest.; vol. 93, 1140-1148 (1994).

Beum, P. V. and Cheng, Pi-W.; "Biosynthesis and Function of β1,6 Branched Mucin-Type Glycans"; The Molecular Immunology of Complex Carbohydrates-2 (2001).

Beum, P. V., et al; "Mucin biosynthesis: upregulation of core 2 β1,6 N-acetylglucosaminyltransferase by retinoic acid and Th2 cytokines in a human airway epithelial cell line"; Am J. Physiol Lung Cell Mol Physiol.; 288: L116-L124 (2005).

Beum, P. V., et al; "Mucin Biosynthesis Epidermal Growth Factor Downregulates Core 2 Enzymes in a Human Airway Adenocarcinoma Cell Line"; Am. J. Respir. Cell Mol. Biol.; vol. 29, 48-56 (2003).

Celie, J.W.A.M, et al; "Identification of L-Selectin Binding Heparan Sulfates Attached to Collagen Type XVIII"; J. Biol Chem.; 280(29); 26965-73; Epub (2005).

Dennis, James W.; "Glyco-Forum Section; Core 2 GlcNAc-Transferase and polylactosamine expression in O-glycans", Glycobiology; vol. 3, No. 2, pp. 91-96 (1993).

Dube, Danielle H. et al, "Glycans in Cancer and Inflammation—Potential for Therapeutics and Diagnostics", Nature Reviews, vol. 4, No. 6, 477-288 (2005).

Duan L-L. et al; "Regulation of Metastasis-Suppressive Gene Nm23-H1 on Glycosy-transferases Involved in the Synthesis of Sialy Lewis Antigens"; J. Cell. Biochem.; 94:1248-1257 (2005).

Fox, R.I., et al; "A Novel Cell Surface Antigen (T305) Found in Increased Fequency on Acute Leukemia Cells and in Autommune Disease States"; J. Immunol. vol. 131, No. 2, 761-767 (1983).

Foxall, C. et al; "The Three Members of the Selectin Receptor Family Recognize a Common Carbohydrate Epitope, the Sialyl Lewis$^x$ Oligosaccharide"; J. Cell Biol.; vol. 117, 895-902 (1992).

Fugang P. et al.; "Post Translational Modifications of Recombinant P-selectin Glycoprotein Ligand-1 Required for Binding to P and E-selectin"; J. Biol. Chem.; vol. 271, No. 6, 3255-3264 (1996).

Fujita, M. et al; "Pulmonary hypertension in TNF-α-overexpressing mice is associated with decreased VEGF gene expression"; J. Applied Physiol; vol. 93, 2162-2170 (2002).

Goss, P. E. et al; "Inhibitors of Carbohydrate Processing: A New Class of Anticancer Agents[1,2]"; Clin. Cancer Res.; vol. 1, 935-944 (1995).

Maaheimo,Hannu et al, "Synthesis of a divalent sialyl Lewis x O-glycan, a potent inhibitor of lymphocyte-endothelium adhesion"; Eur J. Biochem; 234, 616-625 (1995).

Hiraoka, N. et al; "Core 2 Branching β1,6-N-Acetylglucosaminyltransferase and High Endothelial Venule-restricted Sulfotransferase Collaboratively Control Lymphocyte Homing"; J. Biol Chem.; vol. 279, No. 4, 3058-3067 (2004).

Kumar, A. et al; "Recombinant Soluble Form of PSGL-1 Accelerates Thrombolysis and Prevents reocclusion in a Porcine Model"; Circulation; 99, 1363-1369 (1999).

Jain, Rakesh K. et al, "Inhibition of L-and P-selectin by a rationally synthesized novel core 2-like branched structure containing GalNAc-Lewis$^x$ and Neu5Acα2-3Galβ1-3GalNAc sequences"; Glycobiology, vol. 8, No. 7; 707-717 (1998).

Jones, Steven P., "A Bittersweet Modification O-GlcNAc and Cardiac Dysfunction"; Circ Res.; 96; 925-926 (2005).

Kamisako, Toshinori et al, "Regulation of biliary cholesterol secretion is associated with abcg5 and abcg8 expressions in the rats: effects of diosgenin and ethinyl estradiol", Hepatology Research 26; 348-352 (2003).

Lewis, M.J. and D 'Cruz D.; "Adhesion molecules, mycophenolate mofetil and systemic lupus erythematosus"; Lupus, 14, 17-26 (2005).

Martininez, M. et al; "Regulation of PSGL-1 Interactions with L-selectin, P-selectin, and E-selectin"; J. Biol. Chem., vol. 280, No. 7, 5378-5390 (2005.).

Merzaban, Jasmeen S. et al.; "An Alternate Core 2 β,6-N-Acetylglucosaminyltransferase Selectively Contributes to P-Selectin Ligand Formation in Activated CD8 T Cells[1]"; The Journal of Immunology, 174: 4051-4059 (2005).

Morin, M.J. and Bernacki, R.J.; "Biochemical Effects and Therapeutic Potential of Tunicamycin in Murine L1210 Leukemia"; Cancer Res. 43, 1669-1674 (1983).

Nakamura, M. et al.; "Single Glycosyltransferase, Core 2β1-6-N-acetylglucosaminyltransferase, Regulates Cell Surface Sialy-Le$^x$ Expression Level in Human Pre-B Lymphocytic Leukemia Cell Line KM3 Treated with Phorbolester"; J. Biol. Chem.; 273, No. 41; 26779-26789 (1998).

Narumi, S. et al; "Tissue-Specific Induction of E-Selectin in Glomeruli is Augmented following Diabetes mellitus"; Nephron; 89, 161-171 (2000).

Okada, S. et al; "Intercellular Adhesion Molecule-1-Deficient Mice are Resistant Against Renal Injury After Induction of Diabetes"; Diabetes; 52:2586-2593 (2003).

Piccio L. et al; "Molecular Mechanisms Involved in Lymphocyte Recruitment in Inflamed Brain Microvessels: Critical Roles for P-Selectin Glycoprotein Ligand-1 and Heterotrimeric G$_i$-Linked Receptors[1]"; J. Immunol., 168: 1940-1949 (2002).

Ravnskov, U.; "Is atherosclerosis caused by high cholesterol?", Q J Med; 95, 397-403 (2002).

Ross, Russell; "Atherosclerosis—An Inflammatory Disease", The New England Journal of Medicine, vol. 340, 2, 115-126 (1999).

Simmons, Rex D. and Brenda A. Cattle; "Sialyl Ligands facilitate lymphocyte accumulation during inflammation of the central nervous system", Journal of Neuroimmunology, 41; 123-130 (1992).

Steinberg, D.; "Atherogenesis in perspective: Hypercholesterolemia and inflammation as partners in crime"; Nature Medicine; vol. 8, No. 11; 1211-1217 (2002).

Steinman, Lawrence; "Blocking Adhesion Molecules as Therapy for Multiple Sclerosis: Natalizumab"; Nature Reviews: Drug Discovery, vol. 4, 510-518 (2005).

Baek, Suk Hwan, et al, "Inactivation of Human Pleural Fluid Phospholipase A$_2$ by Dioscin"; Arch. Pharm. Res.; vol. 17, No. 4, 218-222 (1994).

Ulbrich, Holger, et al; "Leukocyte and endothelial cell adhesion molecules as targets for therapeutic interventions in inflammatory disease"; *Trends in Pharmacological Sciences*, vol. 24, No. 12; 640-647 (2003).

Williams, D. et al; "Mucin Synthesis II. Substrate Specificity and Product Identification Studies on Canine Submaxillary Gland UDP-GlcNAc:Galβ1-3GalNAc(GlcNAc—GalNAc) β6-*N*-acetylglucosaminyltransferase"; *J. Biol. Chem.*; 255, No. 23; 1253-1261 (1980).

Yanagihara, K., et al; "Lipopolysaccharide Induces Mucus Cell Metaplasia in Mouse Lung"; *Am. J. Respir. Cell Mol. Biol.*; 24, 66-73 (2001).

Zak, I., et al; "Selectin Glycoprotein Ligands"; *Acta Biochemica Polonica*; vol. 47, No. 2; 393-412 (2000).

Davies, Michael J., et al; "The Expression of the Adhesion Molecules Icam-1, Vcam-1, Pecam, and E-Selectin in Human Atherosclerosis", *Journal of Pathology*, vol. 171: 223-239 (1993).

Ke, Hu et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).

Examination Report of Equivalent European Patent Application No. EP 06 755 720.7-2404; dated Sep. 3, 2010 (3 pgs).

Dedrick, R.L., et al; "Adhesion molecules as therapeutic targets for autoimmune diseases and transplant rejection"; *Expert Opinion Biol. Ther.*; vol. 3(1); pp. 85-95 (2003).

Ross, R., "Atherosclerosis—An Inflammatory Disease"; *New England Journal of Medicine*; vol. 340, No. 2; pp. 115-126 (1999).

Guray, U., et al.; "Poor coronary collateral circulation is associated with higher concentrations of soluble adhesion molecules in patients with single-vessel disease"; *Coronary Artery Disease*; vol. 15, No. 7; pp. 413-417 (2004).

Guray, U., et al; "Levels of soluble adhesion molecules in various clinical presentations of coronary atherosclerosis"; *International Journal of Cardiology*; vol. 96; pp. 235-240 (2004).

Hansen, A., et al; "Evaluation of Cardioprotective Effects of Recombinant Soluble P-Selectin Glycoprotein Ligand-Immunoglobulin in Myocardial Ischemia-Reperfusion Injury by Real-Time Myocardial Contrast Echocardiography"; *Journal of the American College of Cardiology*; vol. 44, No. 4; pp. 887-891 (2004).

Hurwitz, A.A., et al; "Tumor Necrosis Factor α Induces Adhesion Molecule Expression on Human Fetal Astrocytes"; *J. Exp. Med.*; vol. 176; pp. 1631-1636 (1992).

Koya, D., et al; "Overexpression of core 2 N-aetylglycosaminyltransferase enhances cytokine actions and induces hypertrophic myocardium in transgenic mice"; *The FASEB Journal*; vol. 13; pp. 2329-2337 (1999).

Kumar, R., et al; "Core2 β-1,6-N-Acetylglucosaminyltransferase Enzyme Activity is Critical for P-Selectin Glycoprotein Ligand-1 Binding to P-Selectin"; *Blood*; vol. 88, No. 10; pp. 3872-3879 (1996).

Lasky, L.A., et al; "Selectin-Carbohydrate Interactions and the Initiation of the Inflammatory Response"; *Annual Review of Biochemistry*; vol. 64; pp. 113-139 (1995).

McMurray, R.W.; "Adhesion Molecules in Autoimmune Disease"; *Seminars in Arthritis and Rheumatism*; vol. 25, No. 4; pp. 215-233 (1996).

Mulvihill, N.T., et al; "Inflammation in acute coronary syndromes"; *Heart*; vol. 87; pp. 201-204 (2002).

Myers, D., et al; "New and Effective Treatment of Experimentally Induced Venous Thrombosis with Anti-inflammatory rPSGL-lg"; *Thromb Haemost*; vol. 87; pp. 374-382 (2002).

Nishio, Y., et al; "Identification and Characterization of a Gene Regulating Enzymatic Glycosylation which is Induced by Diabetes and Hyperglycemia Specifically in Rat Cardiac Tissue"; *J. Clin. Invest.*; vol. 96; pp. 1759-1767 (1995).

O'Brien, K.D., et al; "Neovascular Expression of E-Selectin, Intercellular Adhesion Molecule-1, and Vascular Cell Adhesion Molecule-1 in Human Atherosclerosis and Their Relation to Intimal Leukocyte Content"; *Circulation*; vol. 93, No. 4; pp. 672-682 (1996).

Pillar, F., et al; "Human T-lymphocyte Activation is Associated with Changes in *O*-Glycan Biosynthesis"; *The Journal of Biological Chemistry*; vol. 263, No. 29; pp. 15146-15150 (1988).

Wang, K., et al; "Recombinant Soluble P-Selectin Glycoprotein Ligand-1g (rPSGL-1g) Attenuates Infract Size and Myeloperoxidase Activity in a Canine Model of Ischemia-Reperfusion"; *Thrombosis and Haemostasis*; vol. 88(1); pp. 149-154 (2002).

Confavreux, C., et al; "Age at disability milestones in multiple sclerosis"; *Brain*; vol. 129; pp. 595-605 (2006).

Confavreux, C., et al; "Natural history of multiple sclerosis: a unifying concept"; *Brain*, vol. 129; pp. 606-616 (2006).

Elovaara, I., et al; "Adhesion Molecules in Multiple Sclerosis"; *Arch Neurol*; vol. 57, pp. 546-551 (2000).

McDonnell, G.V., et al; "Serum soluble adhesion molecules in multiple sclerosis: raised sVCAM-1, sICAM-1 and sE-selectin in primary progressive disease"; *J. Neurol*; vol. 246; pp. 87-92 (1999).

Musso, A.M., et al; "Increased serum levels of ICAM-1, ELAM-1 and TNF-α in inflammatory disorders of the peripheral nervous system"; *Ital. J. Neurol. Sci.*; vol. 15; pp. 267-271 (1994).

Rao, A.V., et al; "The Bioactivity of Saponins: Triterpenoid and Steroidal Glycosides"; *Drug Metabolism and drug interactions*; vol. 17, No. 1-4; pp. 212-235 (2000).

Simmons, R.D., et al; "Sialyl ligands facilitate lymphocyte accumulation during inflammation of the central nervous system"; *Journal of Neuroimmunology*; vol. 41; pp. 123-130 (1992).

Ulbrich, H., et al; "Leukocyte and endothelial cell adhesion molecules as targets for therapeutic interventions in inflammatory disease"; *Trends in Pharmacological Sciences*; vol. 24, No. 12; pp. 640-647 (2003).

VanderElst, I.E., et al; "β1,6 N-Acetylglucosaminyltransferase (core 2 GlcNAc-T) expression in normal rat tissues and different cell lines: evidence for complex mechanisms of regulation"; *Glycobiology*, vol. 8, No. 7; pp. 731-740 (1998).

Washington, R., et al; "Expression of Immunologically Relevant Endothelial Cell Activation Antigens on Isolated Central Nervous System Microvessels from Patients with Multiple Sclerosis"; *Annals of Neurology*; vol. 35, No. 1; pp. 89-97 (1994).

\* cited by examiner

CORE 2 β(1,6)-ACETYLGLYCOSAMINYLTRANSFERASE AS DIAGNOSTIC MARKER FOR ATHEROSCLEROSIS

This application is the U.S. National Phase of International Application PCT/GB2006/002502, filed 6 Jul. 2006, which designated the U.S. PCT/GB2006/002502 claims priority to British Application No. 0513883.9 filed 6 Jul. 2005. The entire content of these applications are incorporated herein by reference.

The present invention is made in the field of methods for the diagnosis of vascular disease and in particular atherosclerosis.

BACKGROUND OF THE INVENTION

Atherosclerosis (AS) is known to have an inflammatory component and Core 2 GlcNAc-T (also known as UDP-GlcNAc:Galβ1,3GalNAc-R (GlcNAc to GalNAc) β-1,6 N-acetylaminotransferase or Core 2 β-1,6 N-acetylaminotransferase—EC 2.4.1.102) has been implicated in inflammation (WO 0031109). It has been speculated that Core 2 GlcNAc-T inhibitors may be useful in AS (e.g. WO0185748), however, no published studies have examined the levels of Core 2 GlcNAc-T in patients suffering atherosclerosis nor has the level of this enzyme been suggested as a marker for atherosclerosis in a subject.

SUMMARY OF THE INVENTION

The present inventors have surprisingly found that, the level of Core 2 GlcNAc-T activity in blood samples from patients with atherosclerosis is markedly raised compared to non afflicted healthy individuals consequently levels of Core 2 GlcNAc-T may be used to indicate the presence of atherosclerosis in a subject.

Blood samples may be particularly isolated preparations containing Polymorphonuclear Cells—PMNs and other leukocyte sub-populations and more particularly isolated preparations containing PMNs and Peripheral Blood Mononuclear Cells—PBMCs.

Atherosclerosis includes (coronary artery atherosclerosis/coronary artery disease—CAD/Ischemic Heart Disease—IHD/Arteriosclerotic Cardiovascular Disease —ASCVD/Coronary Heart Disease—CHD)

Accordingly a first aspect of the present invention provides a method of indicating the presence of atherosclerosis in a subject comprising comparing the level of Core 2 GlcNAc-T in a tissue sample from a subject with a reference level determined for the same tissue. A level of Core 2 GlcNAc-T in the tissue sample from a subject that is higher than the reference level being indicative that the subject is afflicted with atherosclerosis.

Typically the reference level is established in the tissue by determining the mean level of Core 2 GlcNAc-T in samples of the tissue from a population of one or more individuals associated with an absence of AS; preferably the reference level is established in the tissue by determining the mean level of Core 2 GlcNAc-T in samples of the tissue from a population of 5 or more individuals associated with an absence of AS; more preferably the reference level is established in the tissue by determining the mean level of Core 2 GlcNAc-T in samples of the tissue from a population of 10 or more individuals associated with an absence of AS Conveniently the tissue sample is a blood sample.

Conveniently the level of Core 2 GlcNAc-T may be determined in Leukocytes which may be isolated from blood by methods well known in the art.

Particularly level of Core 2 GlcNAc-T may be determined in isolated preparations containing PMNs and other leukocyte sub-populations and more particularly in isolated preparations containing PMNs and PBMCs The level of Core 2 GlcNAc-T may be the level of Core 2 GlcNAc-T RNA transcript, the level of Core 2 GlcNAc-T protein or the level of Core 2 GlcNAc-T enzyme activity; preferably it is the level of Core 2 GlcNAc-T enzyme activity.

Suitable assays for Core 2 GlcNAc-T enzyme activity include those using radio-labelled substrates or acceptor compounds, using fluorescently labelled substrates or acceptor compounds, or by derivatising a formed product prior to analysis (eg by HPLC) for example those described herein or in Chibber et al *Diabetes* 49, 1724-1730 (2000), Palmerini C. A. et al *Glycoconj J.* August; 13(4):631-6 (1996) or Kuhns W. et al *Glycoconjugate Journal* 10 381-394 (1993) (all of which are incorporated herein by reference). Leukocytes may be isolated from blood samples and the Core 2 GlcNAc-T activity determined as described in Chibber et al (2000) or by the protocol described herein under example 1.

The inventors have determined that the level of Core 2 GlcNAc-T enzyme activity in leukocyte preparations obtained from healthy individuals and assayed by the method of Chibber et al (2000) or as detailed in Example 1 is between 40 and 1000 pmoles/hr/mg protein and typically between 50 and 500 pmoles/hr/mg of protein.

The mean value may be between 50 and 1000, typically between 100 and 500 and more typically between 200 and 400 pmoles/hr/mg.

Levels of Core 2 GlcNAc-T in individuals afflicted with atherosclerosis will be in the region of at least 2 times, preferably at least 4 times, more preferably at least 6 times and most preferably at least 8 times the reference level of healthy non afflicted individuals when blood samples are treated and leukocytes assayed according to Chibber et al (2000) or as detailed in example 1.

The method of the invention can conveniently be carried out using a kit comprising components necessary for carrying out the method of the invention. Thus in a second embodiment of the invention is provided a kit for indicating the presence of atherosclerosis in a subject. The kit will preferably comprise an acceptor compound. An acceptor compound is a compound to which Core 2 GlcNAc-T is capable of transferring a monosaccharide residue. Preferably the acceptor compound is a derivative of Galβ(1,3)GalNAcα. Suitable acceptor compounds are for example Galβ(1,3)GalNAc-Bn, Galβ(1,3)GalNAc-p-nitrophenol or Galβ(1,3)GalNAcα-p-NHdansylphenyl.

Optionally the kit will also comprise UDP-GlcNAc, which may be radiolabelled. Conveniently the UDP-GlcNAc is labelled by $^{14}C$ or $^{3}H$. Optionally the kit may further contain N-Acetylglucosamine (GlcNAc) and reagents for lysing leukocytes, such as a detergent (for example Triton-X100). The kit may comprise instructions for its use.

The present invention will now be described further by reference to the following non-limiting Examples, Schemes and Figures. Further embodiments falling within the scope of the claim will occur to those skilled in the art in the light of these

EXAMPLES

Figure 1:
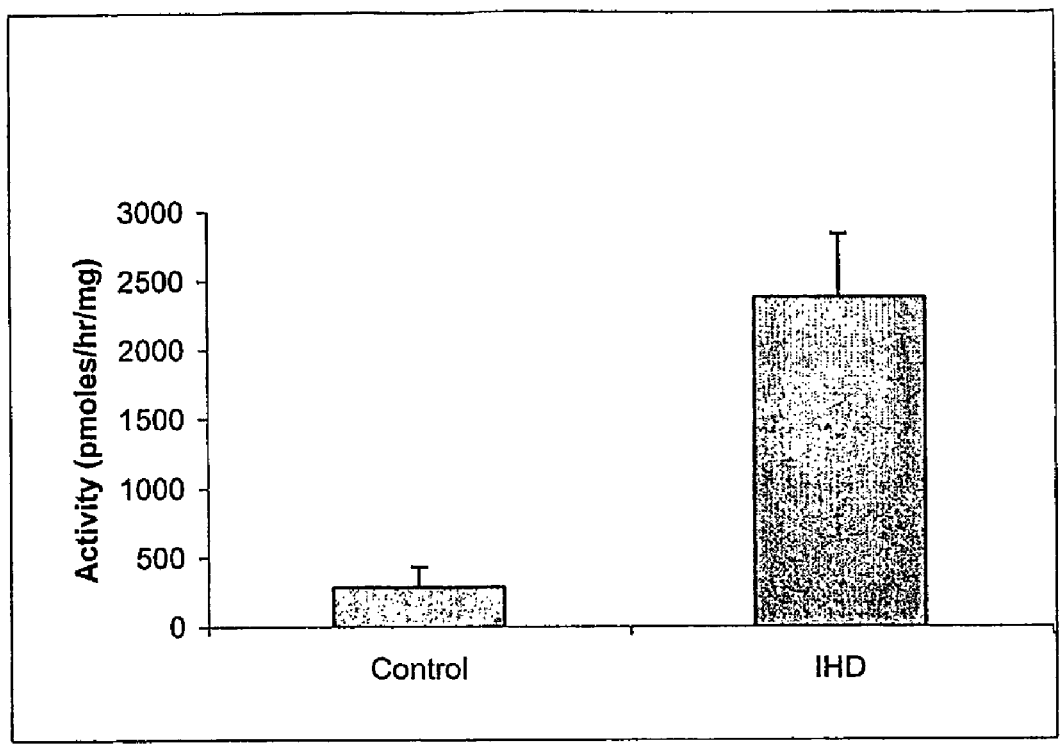
FIG. 1 is a graph illustrating the levels of Core 2 GlcNAc-T activity in leukocytes from healthy control individuals and subjects with ischaemic heart disease (IHD). For controls n=19 for IHD patients n=13.

1. Determination of Core 2 GlcNAc-T Activity in Leukocvtes Isolated from the Blood of Patients Diagnosed with Ischemic Heart Disease 13 Middle aged patients of both genders with IHD and 19 age matched healthy controls were used in this study. Patients with diabetes were excluded. IHD patients included in the study suffered stable angina, unstable angina, or had recently suffered a myocardial infarction.

Blood was taken into heparinised tubes. The blood sample was layered onto an equal volume of HISTO-PAQUE 1077 (Pharmacia and available from Sigma, Poole, Dorset, UK) and centrifuged at 400 g for 30 mins. The Buffy coat (containing peripheral blood mononuclear cells (PBMNC) and polymorphonuclear (PMN) leukocytes) was washed in phosphate buffered saline. Isolated leukocytes were frozen and lysed in 0.9% NaCl 0.4% Triton-X100 1 mM PMSF and the Core 2 GlcNAc-T assayed. The reaction was performed in 50 mmol/l 2(N-morpholino) 2(N-morpholino) ethanesulfonic acid pH 7.0; 1 mmol/l UDP GlcNAc, 0.5 µCi UDP-6 [3H]-N-acetylglucosamine (16,000 dpm/nmol, NEN Life Science Products, Hounslow, U.K.); 0.1 mol/l GlcNAc; 1 mmol/l βgal (1-3)Da-GalNAc-p-nitrophenol and 15 µl cell lysate (100-200 µg protein) for a final volume of 30 µl. After incubating the mixture for 1 h at 37° C., the reaction was terminated by adding 1 ml of ice cold water and processed on a C18 SEP-PAK column (Waters-Millipore, Watford, U.K.). After washing the column with 20 ml water, the product was eluted with 5 ml methanol and radioactivity counted. Endogenous activity of Core 2 GlcNAc-T was measured in the absence of the added acceptor. The results are shown in FIG. 1.

Core 2 GlcNAc-T activity in healthy individuals was 287±147.2 pmoles/hr/mg or protein, whist in patients with IHD the value was 2376±461. These values are in agreement with those for three groups of healthy individuals in Chibber et al (2000) in which values were 249±35.9 (n=25), 334±86 (n=11) and 283±37 (n=31) pmols/hr/mg.

The invention claimed is:

1. A method of indicating possible atherosclerosis in a subject comprising comparing the level of Core 2 GlcNAc-T enzyme activity in a blood sample from a subject with a reference enzyme activity level determined for a blood sample, wherein a level of Core 2 GlcNAc-T enzyme activity in the blood sample from a subject that is higher than the reference enzyme activity level being indicative that the subject may be afflicted with atherosclerosis.

2. A method according to claim 1 wherein the level of core 2 GlcNac-T enzyme activity is measured in leukocytes.

3. A method according to claim 2 in which the leukocytes are isolated from the blood.

4. A method according to claim 2 wherein a level of Core 2 GlcNAc-T enzyme activity of the leukocytes of a subject is at least 2 times higher than that of the reference level is indicative of atherosclerosis in the subject.

5. A method according to claim 2 wherein a level of Core 2 GlcNAc-T enzyme activity of the leukocytes of a subject is at least 4 times higher than that of the reference enzyme activity level is indicative of atherosclerosis in the subject.

6. A method according to claim 2 wherein a level of Core 2 GlcNac-T enzyme activity of the leukocytes of a subject is at least 2 times higher than that of the reference enzyme activity is indicative of atheroscleosis in the subject.

7. A method according to claim 2 wherein a level of Core 2 GlcNAc-T enzyme activity of the leukocytes of a subject is at least 8 times higher than that of the reference level is indicative of atherosclerosis in the subject.

* * * * *